(12) United States Patent
Aljohani

(10) Patent No.: US 9,381,292 B2
(45) Date of Patent: Jul. 5, 2016

(54) DIABETES REGULATOR

(71) Applicant: Kamal Ahmed Aljohani, Melbourne, FL (US)

(72) Inventor: Kamal Ahmed Aljohani, Melbourne, FL (US)

( * ) Notice: Subject to any disclaimer, the term of this patent is extended or adjusted under 35 U.S.C. 154(b) by 148 days.

(21) Appl. No.: 14/339,984

(22) Filed: Jul. 24, 2014

(65) Prior Publication Data

US 2016/0022899 A1    Jan. 28, 2016

(51) Int. Cl.
| | | |
|---|---|---|
| *A61M 1/36* | (2006.01) | |
| *A61K 38/28* | (2006.01) | |
| *A61K 38/26* | (2006.01) | |
| *A61M 1/34* | (2006.01) | |
| *A61K 35/39* | (2015.01) | |

(52) U.S. Cl.
CPC .............. *A61M 1/3689* (2014.02); *A61K 35/39* (2013.01); *A61K 38/26* (2013.01); *A61K 38/28* (2013.01); *A61M 1/34* (2013.01); *A61M 2205/04* (2013.01); *A61M 2205/75* (2013.01); *A61M 2230/201* (2013.01); *C12N 2510/02* (2013.01)

(58) Field of Classification Search
CPC ............................... A61F 2/04; A61M 1/3689
USPC ........................................... 623/23.64–23.65
See application file for complete search history.

(56) References Cited

U.S. PATENT DOCUMENTS

| | | | | |
|---|---|---|---|---|
| 6,122,536 | A * | 9/2000 | Sun | A61B 5/0031 600/317 |
| 7,531,120 | B2 * | 5/2009 | Van Rijn | A61L 27/50 264/299 |
| 8,021,130 | B2 * | 9/2011 | Votaw | B01L 3/50273 417/32 |
| 9,101,707 | B2 * | 8/2015 | Zeltser | A61M 5/14276 |
| 2004/0028875 | A1 * | 2/2004 | Van Rijn | A61L 27/50 428/98 |
| 2010/0010479 | A1 * | 1/2010 | Erickson | A61M 5/14216 604/891.1 |
| 2013/0090534 | A1 * | 4/2013 | Burns | A61B 3/16 600/301 |
| 2013/0137591 | A1 * | 5/2013 | Clemens | G01N 27/27 506/9 |

(Continued)

FOREIGN PATENT DOCUMENTS

| | | |
|---|---|---|
| WO | WO 98/57701 | 12/1998 |
| WO | WO 00/53257 | 9/2000 |
| WO | WO 01/66183 A1 | 9/2001 |

OTHER PUBLICATIONS

Pagkalos, I., et al., "An analogue implementation of the beta cell insulin release model", Circuits and Systems (ISCAS), 2013 IEEE International Symposium, May 2013, 1 page.

(Continued)

*Primary Examiner* — Suzette J-J Gherbi
(74) *Attorney, Agent, or Firm* — Oblon, McClelland, Maier & Neustadt, L.L.P.

(57) ABSTRACT

An implantable device that continuously regulates the blood glucose levels of a type 1 diabetes mellitus patient is provided. The device which is implanted in the bloodstream, relies on a microfluidic chip and a microsieve that efficiently separate leukocytes away from an amount of blood received and an islet compartment made up of multiple islets (beta and alpha cells) from at least one compatible donor pancreas source. During hyperglycemia, insulin is produced by the beta cells to remove excessive sugar from the blood. Similarly, during hypoglycemia, glucagon is secreted by the alpha cells to bring the blood glucose level back to normal. The device is self-sustaining without relying on an electrically-powered insulin pump or refills of exogenous insulin.

16 Claims, 3 Drawing Sheets

(56) References Cited

U.S. PATENT DOCUMENTS

| | | | |
|---|---|---|---|
| 2013/0289540 A1* | 10/2013 | Zeltser | A61M 5/14276 604/891.1 |
| 2014/0081384 A1* | 3/2014 | Hoganson | A61F 2/062 623/1.27 |
| 2015/0011847 A1* | 1/2015 | Hayden | A61B 5/15003 600/309 |
| 2015/0119848 A1* | 4/2015 | Chaum | G01N 27/333 604/504 |
| 2015/0297828 A1* | 10/2015 | Zeltser | A61M 5/14276 604/891.1 |
| 2016/0022180 A1* | 1/2016 | Joseph | A61B 5/6852 600/317 |

OTHER PUBLICATIONS

Mine M. Ozyetkin, et al., "A New Robust Nonlinear Control Algorithm for the Regulation of Blood Glucose in Diabetic Patients", 2012 IEEE International Conference on Control Applications, 5 pages.

* cited by examiner

DIABETES REGULATOR

BACKGROUND

Grant of Non-Exclusive Right

This application was prepared with financial support from the Saudia Arabian Cultural Mission, and in consideration therefore the present inventor(s) has granted The Kingdom of Saudi Arabia a non-exclusive right to practice the present invention.

1. Field of the Disclosure

The present invention is directed to a medical device for patients of type 1 diabetes mellitus. More particularly, the disclosed device is an implant that functions to, inter alia, supply insulin into the bloodstream.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Diabetes mellitus is a metabolic disease where blood sugar levels are high over a prolonged period. As of 2013, 382 million people suffer from diabetes mellitus worldwide. In 2012, the disease resulted in 1.5 million deaths globally, making it the eighth leading cause of death.

Type 1 diabetes mellitus (T1DM), formerly known as insulin dependent diabetes or juvenile diabetes, is a form of diabetes mellitus that results from the autoimmune destruction of insulin-producing beta cells in the pancreas. This lack of insulin, in turn, results in increased blood and urine glucose. The cause of T1DM is unknown.

Classic symptoms of T1DM include frequent urination, increased thirst, weight loss despite an increase in appetite, fatigue, nausea and blurred vision. The disease is also fraught with acute and chronic complications. Acute complications include, for example, hyperosmolar coma, ketoacidosis (accumulation of ketone bodies in the body) and hypoglycemia. Chronic complications, on the other hand, include cataract, glaucoma, diabetic retinopathy, kidney damage and nerve damage.

There is no known preventive measure or cure for T1DM, which is also a chronic disease. Unlike type 2 diabetes mellitus which can often be prevented by a generally healthy lifestyle, a T1DM patient must rely on a lifetime of continuous exogenous supply of insulin for survival. This is called insulin therapy, which is treatment of diabetes mellitus by administration of exogenous insulin.

There are various modes of administration in insulin therapy, with subcutaneous injection being the most common. Other modes of administration include insulin pump, inhalation, transdermal, intranasal insulin, oral insulin. The central problem for patients requiring external insulin is picking the right dose of insulin and the right timing. The insulin pump which is a more conventionally used mode of administration, apart from the aforementioned problems, is costly, can be unreliable, uncomfortable and inconvenient.

More invasive and drastic methods of treatment that circumvent the dosage and timing dilemma are pancreatic transplantation and islet cell transplantation. The goal of both transplantation procedures is to create a self-regulating insulin source within a T1DM patient's body. However, overcoming the immune barrier (both alloimmunity and autoimmunity) and the procedures themselves are difficult and complicated.

Latest in the pipeline of technologies developed to treat T1DM is the artificial pancreas that helps patients to automatically control their blood glucose level by providing the substitute endocrine functionality of a healthy pancreas. The artificial pancreas is also sometimes referred to as the "bionic pancreas".

The pancreas is a dual-functional organ featuring both endocrine and exocrine systems. Endocrine functionality is provided by cell clusters called the islets of Langerhans that consist of four main cell types: 1). Alpha cells that secrete glucagon that increases glucose in blood); 2). Beta cells that secrete insulin that decreases glucose in blood; 3). Delta cells that secrete somatostatin that regulates alpha and beta cells; and 4). Gamma or PP cells that secrete pancreatic polypeptides to regulate both endocrine and exocrine secretion activities of the pancreas.

Different approaches in the concept of an artificial pancreas are being explored. The artificial pancreas can manifest as a medical equipment system consisting of a continuous blood glucose sensor and an insulin pump under closed loop control using real-time data. Alternatively, the artificial pancreas can adopt a bioengineering approach in the form of a surgical implant consisting of a biocompatible sheet of encapsulated beta cells. Yet another strategy is gene therapy wherein a patient is infected with a genetically engineered virus which causes a DNA change of intestinal cells to become insulin-producing cells.

In view of the foregoing, it will be advantageous to design an artificial pancreas that can overcome crucial problems limitations like insulin dosage and supply, timing, immune barrier for viable clinical applications.

SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

In one broad aspect, the present invention relates to an implantable device that is self-sustaining for producing a continuous supply of insulin and glucagon comprising three components: (a) a blood separator component comprising a blood inlet to receive an incoming amount of blood from the bloodstream, a microfluidic chip to maintain a density of gradient for the blood flow, the microfluidic chip further comprising a main channel with a microsieve disposed in the middle to separate the blood into a leukocyte-rich blood fraction and a leukocyte-depleted blood fraction and to divide the main channel into first and second bifurcated channels, wherein the leukocyte-depleted blood fraction is transported by the first bifurcated channel into to an islet compartment and the leukocyte-rich blood fraction is transported by the second bifurcated channel into an exiting channel and through a blood outlet to return to the bloodstream; (b) an islet component comprising multiple beta and alpha cells from at least one compatible donor pancreas; wherein the beta and alpha cells are encapsulated within a semi-permeable, biocompatible protecting coating, wherein the blood glucose level in the leukocyte-depleted blood is continuously monitored by the beta and alpha cells, wherein the beta cells are activated to produce an elevated level of insulin during hyperglycemia and the alpha cells are activated to produce and an elevated level of glucagon during hypoglycemia; and (c) an exiting channel comprising a blood outlet to transport leukocyte-depleted blood fraction insulin and/or glucagon secreted by the beta and/or alpha cells of the islet compartment and leukocyte-rich blood fraction out of the device back into the blood stream.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
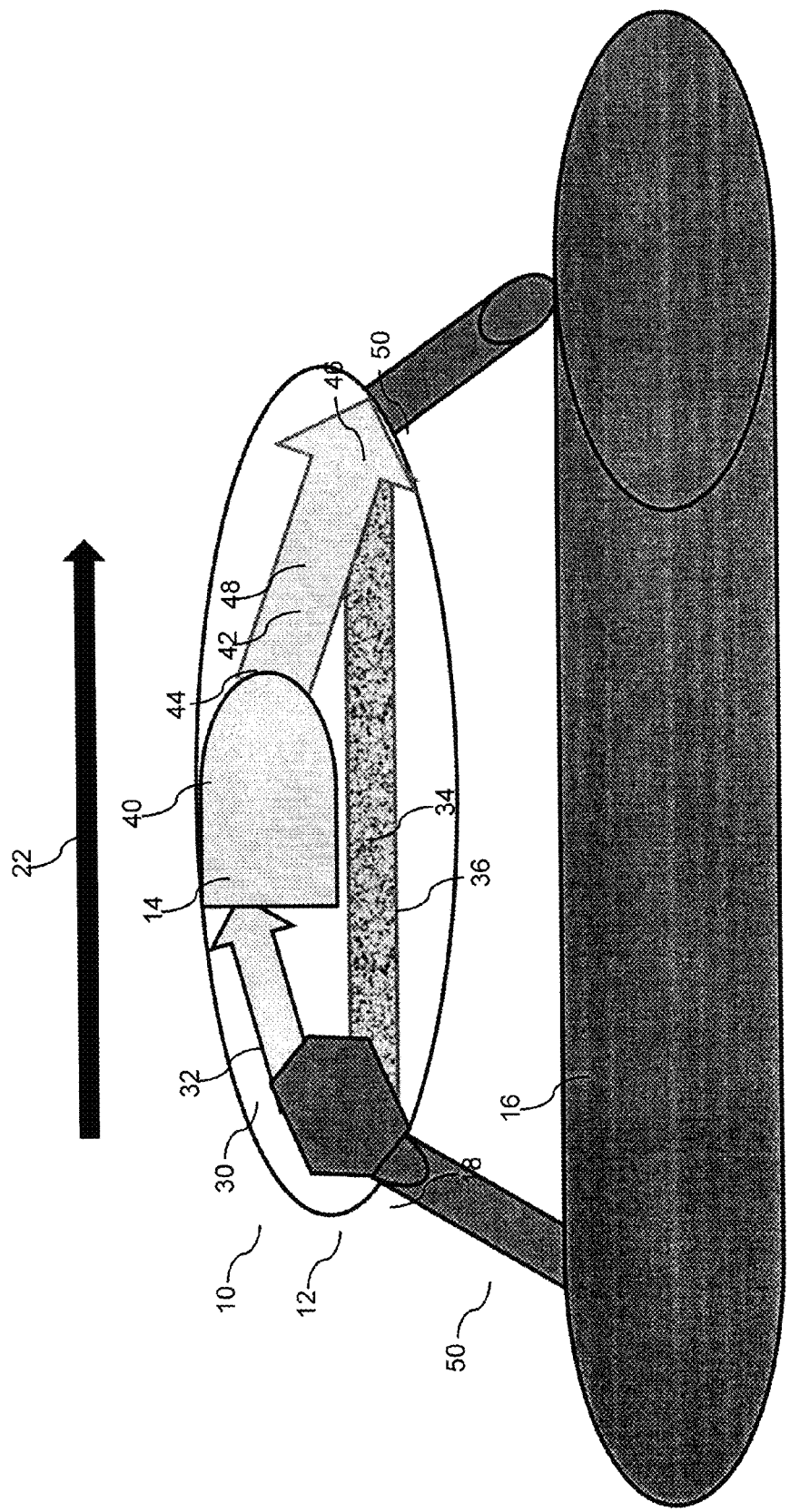
FIG. 1 is a scheme illustrating the various components of an artificial pancreas and their functions according to one embodiment of the present invention.

Referring now to the drawings, wherein like reference numerals designate identical or corresponding parts throughout the several views.

Embodiments of the present invention describe a multi-compartmental diabetes regulator which is an implant for T1DM patients. The device performs three functions simultaneously: 1). Monitoring continuously blood glucose levels at real time; 2). Producing insulin during hyperglycemia; and 3) Producing glucagon during hypoglycemia.

Referring to FIG. 1, diabetes regulating device 10 is composed of blood separator 12 and islet compartment 14. When implanted intraperitoneally in a patient's body and in the bloodstream, device 10 receives a constant blood flow through separator 12 from blood vein 16. In one embodiment, blood vein may be the portal vein. The implantation site of device 10 is flexible as long as it is in the bloodstream. For example, as mentioned above, in some embodiments, device 10 can be implanted intraperitoneally, that is within the peritoneal cavity that contains the abdominal organs. However, it is not necessary that device 10 is placed at or close to the liver and the pancreas. In another embodiment, the device is implanted subdermally, that is under the skin. In yet another embodiment, the device is implanted transdermally, that is partially under the skin and the device is taken out from time to time for cleaning.

Figure 2:
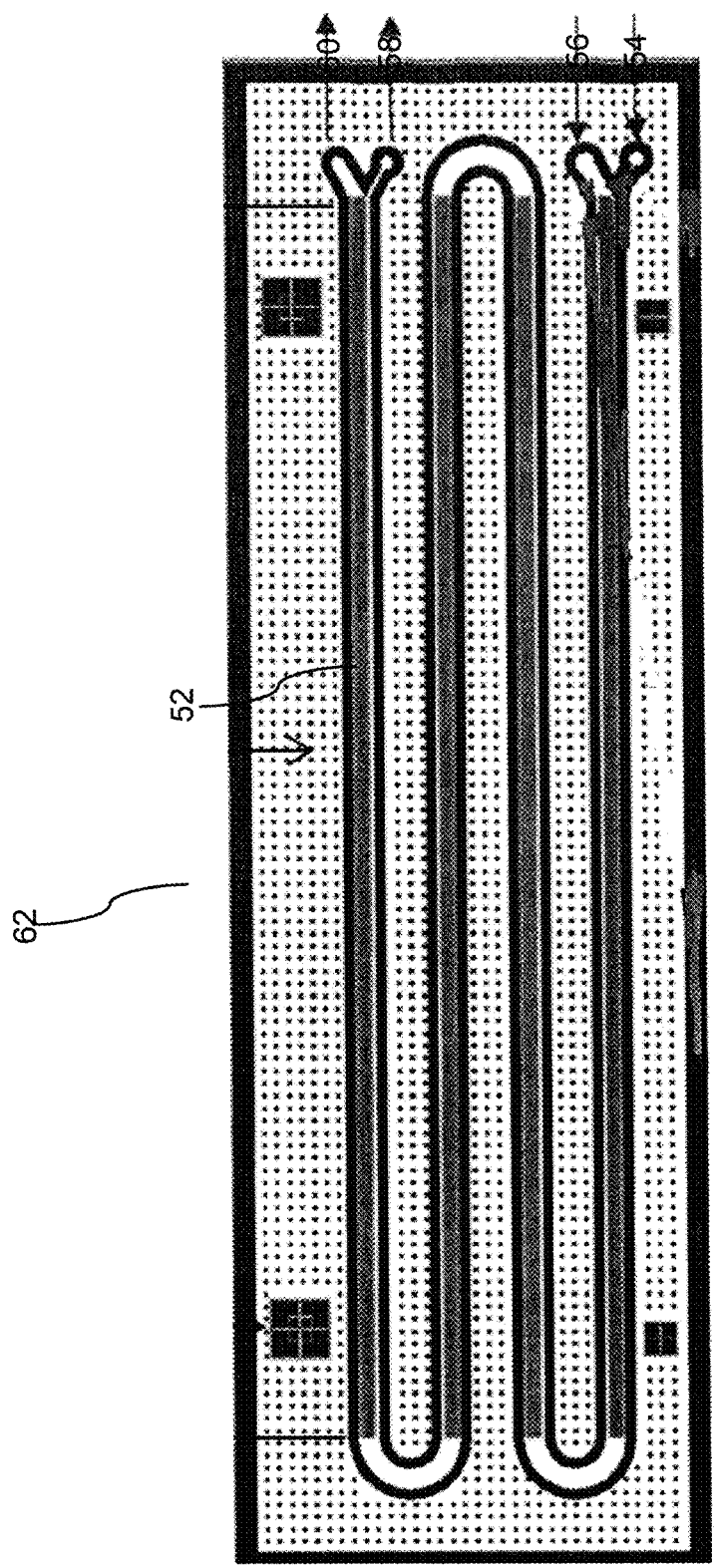
FIG. 2 is an image of a microfluidic device adopting the affinity flow fractionation technique to separate leukocytes from whole blood.

Now referring to FIG. 2, blood separator 12 receives blood flow through blood inlet 18. To ensure a constant and continuous blood flow, density gradient of 1.06-1.10 mg/µl between blood vein 16 and device 10 is generated and maintained by microfluidic chip 20. Constructive materials for microfluidic chip 20 are glass, other silica-containing materials, polymeric materials and optionally metals for electrodes.

Blood continues to flow at a rate of 5 µl min$^{-1}$, as controlled by microfluidic chip 20, in the direction indicated by arrow 22. In one embodiment, the microfluidic chip includes a main channel 24. A micro-fabricated sieve 26 is disposed in the middle of main channel 24. The sieve 26 is made up of round pores of different sizes varying from 5-20, preferably 10-15 micron in diameter. The design of the pores exploits the size and shape difference between red blood cells and white blood cells (neutrophils, eosinophils, basophils, lymphocytes, monocytes) as well as the difference in deformability to deplete the latter. Sieve 26 also creates bifurcated channels 28, 30 at the end of main channel 24. The geometry of bifurcated channels 28, 30 also further enhances the leukapheresis process by maintaining a continuous flow of to prevent the clogging of red and white blood cells. There are different microfluidic techniques for blood component separation in the literature wherein not all are suitable for in vivo uses, like in this present invention. The design of bifurcated channels and a filtering micro-fabricated sieve serves as a passive device that requires no external manipulation.

Channel 28 extends into outlet 30 to transport leukocyte-depleted blood fraction 32 into islet compartment 14 while leukocyte-rich blood fraction 34 is returned to bloodstream 50 via outlet 36 which extends from channel 38. All channels 22, 28, 38 and outlets 30, 36 are made glass and optionally other silica-containing material. This is especially important for channels 38 and outlet 36 containing leukocyte-rich blood fraction 34 to ensure no leukocytes diffuse into islet compartment 14 and destroy the cells in islet compartment 14.

In another embodiment, micropillars that leverage the differences in size and deformability of blood cells is employed for the separation of white blood cells at the microfluidic chip. One emerging technique in this micropillar separation strategy is the deterministic lateral displacement (DLD) wherein the microfluidic device design consists of arrays of micropillar structures placed within the main flow channel leading to the formation of multiple cell streams based on size.

In another embodiment, DLD microfluidic chip comprises an input region, an array region and an output region. The input region has a critical size of 10 micron which is larger than majority of blood cells. The input region consists of a fluidic channel to deliver 25 µl of blood from the bloodstream to the array region for separation. The array region consists of a post and gap size of 10 micron to yield a critical threshold of about 5 micron which is ideal for separation of leukocytes from whole blood. A uniform fluid flow in the array region alongside that of the input stream, is required for DLD microfluid chip to function. A plurality of micropillars delivers the buffer solution to carry and support leukocytes as they are removed from the native blood solution.

Within the array region, blood flows from the input region to the output region, and large cells, which are leukocytes in the case of the present invention, move at a displacement angle with respect to the fluid. With diameter sizes greater than 5 micron, leukocytes were above the critical threshold size for the array region and no longer followed the streamlines. They were instead displaced at an angle within the range of 5.2-5.8°. The displaced leukocytes form the leukocyte-rich blood fraction which is returned to the bloodstream via an outlet which extends from the channel. The remaining erythrocytes, platelets and plasma in the whole blood mixture for leukocyte-depleted blood fraction flows to the output region. The output region consists of a post and gap size of 5 micron, which gives a critical threshold of about 2.5 micron. The output region extends into the outlet to transport the leukocyte-depleted blood fraction into the islet compartment.

In yet another embodiment, the microfluidic device may adopt the affinity flow fractionation (AFF) technique wherein weak, short-range interactions with asymmetric molecular patterns laterally displace cells in a continuous, label-free process. Referring to FIG. 2, the AFF microfluidic device 62 consists of a serpentile channel 52 with two inlet (54, 56) and outlet (58, 60) ports. The device accepts a sample stream of blood or a mixture of cells through blood inlet 54 and a buffer stream through buffer inlet 56, which then run parallel in a 20-cm long serpentile separation channel 52. The cells settle under the influence of gravity along the length of separation channel 52, allowing them to interact with inclined molecular patterns at the bottom of the channel.

Figure 3:
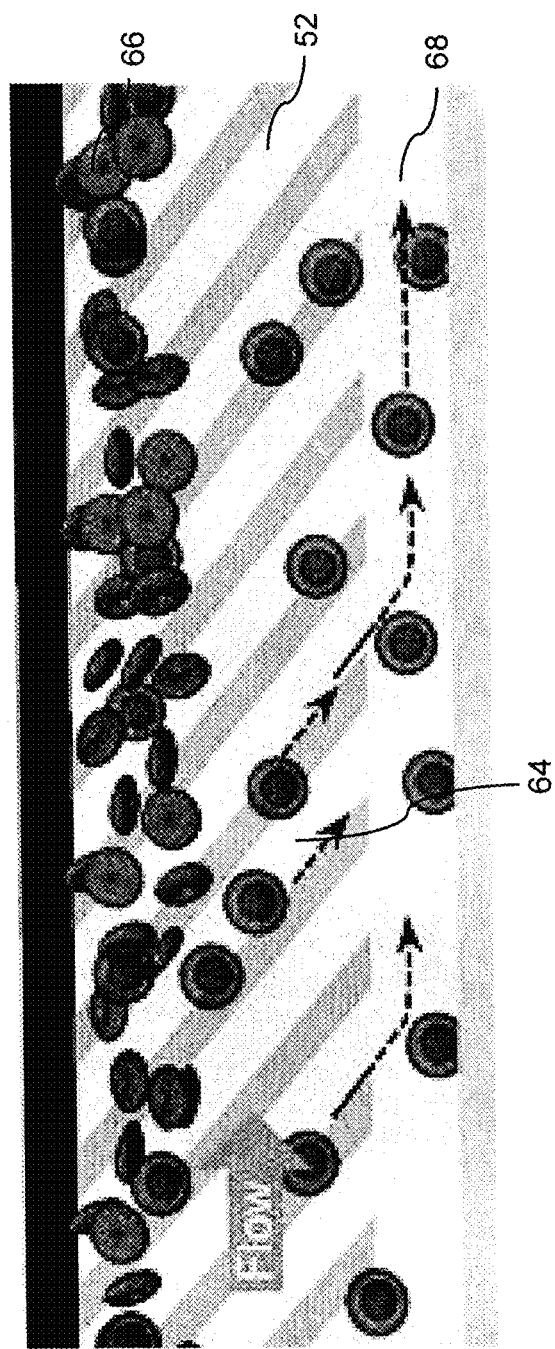
FIG. 3 shows the displacement of leukocytes from whole blood into the buffer stream after the asymmetry of the patterns along the separation channel alters their trajectories.

For sorting of leukocytes, P-selectin patterns comprising parallel strips (15 μm in width) are aligned at 15° to the direction of fluid flow to maximize their lateral displacement, as shown in FIG. 3. The desired pattern may be replicated in gold on a glass slide using photolithography. The gold region may be activated using 3,3-dithiopropionic acid di(N-succinimidyl ester) while the glass may be passivated using PEG-silane, following which the substrate may be incubated with P-selectin solution which leads to immobilization of the P-selectin molecules specifically to the gold region. Target cells like leukocyte 64 that interacts with the P-selectin patterns along separation channel 52 may be displaced laterally from whole blood sample 66 into buffer stream 68 and eventually reaches the non-patterned gutter region that allows for quick elution of the separated cell. The leukocytes which are separated from the rest of the blood components form the leukocyte-rich fraction that elutes through waste outlet 58 and to be returned to the bloodstream. The leukocyte-depleted fraction is eluted through sorted outlet 60 to be transported to islet compartment 14 Islet compartment 14 consists of islets from at least one compatible donor pancreas, including beta and alpha cells. The beta and alpha cells are encapsulated in a protective, biocompatible coating 40 for immunoisolation and to minimize graft rejection. Acceptable constructive materials for the coating include, for example, polyacrylonitrile, polyvinylchloride, nitrocellulose acetate, 2-hydroxyethylmethacrylate (HEMA), acrylonitrile, polyacrylonitrile, sodium methalluosulfonate, alginate, hydrogel, chitosan, agarose, cellulose. These materials allow permeability for hormonal, nutrient and oxygen exchange, but not leukocytes. The source of the hormones, nutrients and oxygen for the viability of the cells in the islet compartment is the leukocyte-depleted blood fraction that passes through the compartment.

Islet compartment 14 serves as an artificial pancreas. Through the insulin and glucagon produced by the beta and alpha cells, respectively, islet compartment serves to monitor glucose levels in leukocyte-depleted blood fraction 32 continuously and maintain the glycemic homeostasis.

In one embodiment, beta cells in islet compartment produce and secrete insulin at a basal level of 0.05 to 2 mg/dL per hour, depending on the blood glucose level. During hyperglycemia, for example, after a meal, blood glucose levels higher than 100 mg/dL are detected by the beta cells of device 10. The beta cells are activated to produce insulin at bolus levels of 0.5 to 20 mg/dL, depending on the increasing rate of blood glucose levels. Elevated levels of insulin secretion inhibit the secretion of glucagon and remove the excessive sugar from the blood. Specifically, insulin-rich leukocyte-depleted blood fraction 42 leaves islet compartment 14 and is transported back into bloodstream 50 via exiting channel 44 and through blood outlet 46. Glucose is catalytically converted and stored as glycogen by the secreted insulin in the liver.

In another embodiment, during a diabetic hypoglycemia episode or a fasting period, blood glucose levels are low. When blood glucose levels fall below 60 mg/dL, alpha cells are activated to produce and secrete glucagon as a negative feedback mechanism response. Glucagon-rich leukocyte-depleted blood fraction 46 is returned to bloodstream 50 via exiting channel 44 and through blood outlet 42. Glycogenolysis and gluconeogenesis are activated, as catalyzed by glucagon, to produce glucose to bring blood glucose levels up to a normal level of 70-100 mg/dL.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A device for producing a supply of insulin and glucagon, implanted on or in a human in need of treatment for type 1 diabetes, comprising:
   (a) a blood separator component comprising a blood inlet to receive incoming blood from a bloodstream of the human,
   a microfluidic chip to maintain a density gradient for a blood flow inside the blood separator,
   the microfluidic chip comprising a main channel with a microsieve to separate the blood flow into a leukocyte-rich blood fraction and a leukocyte-depleted blood fraction and to divide the main channel into first and second bifurcated channels,
   the microsieve comprising a plurality of round pores of 5-20 micron in diameter length,
   wherein the leukocyte-depleted blood fraction is transported by the first bifurcated channel into an islet compartment and the leukocyte-rich blood fraction is transported by the second bifurcated channel into an exiting channel and through a blood outlet to return to the bloodstream;
   (b) an islet compartment comprising multiple beta and alpha cells from at least one compatible donor pancreas;
   wherein the beta and alpha cells are encapsulated within a semi-permeable, biocompatible protecting coating,
   wherein the blood glucose level in the leukocyte-depleted blood is continuously monitored by the beta and alpha cells in real time,
   wherein the beta cells produce an elevated level of insulin during hyperglycemia and the alpha cells produce an elevated level of glucagon during hypoglycemia; and
   (c) an exiting channel comprising a blood outlet to transport the leukocyte-depleted blood fraction, insulin and/or glucagon secreted by the beta and/or alpha cells of the islet compartment and leukocyte-rich blood fraction out of the device back into the blood stream of the human.

2. The implantable device of claim 1, wherein the density gradient for the blood flow inside the blood separator is maintained at 1.06-1.10 mg/ul.

3. The implantable device of claim 1, wherein the semi-permeable, biocompatible protecting coating encapsulating the beta and alpha cells comprises at least one material selected from the group consisting of polyacrylonitrile, polyvinylchloride, nitrocellulose acetate, 2-hydroxyethylmethacrylate (HEMA), acrylonitrile, polyacrylonitrile, sodium methalluosulfonate, alginate, hydrogel, chitosan, agarose, and cellulose.

4. The implantable device of claim 1, wherein the microsieve further comprises a plurality of round pores of 10-15 micron in diameter length.

5. The implantable device of claim 1, wherein the leukocyte count of the leukocyte-depleted blood fraction is less than $4\times10^9$/L.

6. The implantable device of claim 1, wherein the beta cells are activated to produce an elevated level of insulin when a blood glucose level of more than 100 mg/L is detected.

7. The implantable device of claim 1, wherein the alpha cells are activated to produce an elevated level of glucagon when a blood glucose level of less than 60 mg/L is detected.

8. A device for producing a supply of insulin and glucagon, implanted on or in a human in need of treatment for type 1 diabetes, comprising:
(a) a blood separator component comprising a blood inlet to receive incoming blood from a bloodstream of the human,
a microfluidic chip to maintain a density gradient for a blood flow inside the blood separator,
the microfluidic chip comprising a main channel with a microsieve to separate the blood flow into a leukocyte-rich blood fraction and a leukocyte-depleted blood fraction and to divide the main channel into first and second bifurcated channels,
wherein the leukocyte count of the leukocyte-depleted blood fraction is less than $4\times10^9$/L,
wherein the leukocyte-depleted blood fraction is transported by the first bifurcated channel into an islet compartment and the leukocyte-rich blood fraction is transported by the second bifurcated channel into an exiting channel and through a blood outlet to return to the bloodstream;
(b) an islet compartment comprising multiple beta and alpha cells from at least one compatible donor pancreas;
wherein the beta and alpha cells are encapsulated within a semi-permeable, biocompatible protecting coating,
wherein the blood glucose level in the leukocyte-depleted blood is continuously monitored by the beta and alpha cells in real time,
wherein the beta cells produce an elevated level of insulin during hyperglycemia and the alpha cells produce an elevated level of glucagon during hypoglycemia; and
(c) an exiting channel comprising a blood outlet to transport the leukocyte-depleted blood fraction, insulin and/or glucagon secreted by the beta and/or alpha cells of the islet compartment and leukocyte-rich blood fraction out of the device back into the blood stream of the human.

9. The implantable device of claim 8, wherein the density gradient for the blood flow inside the blood separator is maintained at 1.06-1.10 mg/ul.

10. The implantable device of claim 8, wherein the semi-permeable, biocompatible protecting coating encapsulating the beta and alpha cells comprises at least one material selected from the group consisting of polyacrylonitrile, polyvinylchloride, nitrocellulose acetate, 2-hydroxyethylmethacrylate (HEMA), acrylonitrile, polyacrylonitrile, sodium methalluosulfonate, alginate, hydrogel, chitosan, agarose, and cellulose.

11. The implantable device of claim 8, wherein the beta cells are activated to produce an elevated level of insulin when a blood glucose level of more than 100 mg/L is detected.

12. The implantable device of claim 8, wherein the alpha cells are activated to produce an elevated level of glucagon when a blood glucose level of less than 60 mg/L is detected.

13. A device for producing a supply of insulin and glucagon, implanted on or in a human in need of treatment for type 1 diabetes, comprising:
(a) a blood separator component comprising a blood inlet to receive incoming blood from a bloodstream of the human,
a microfluidic chip to maintain a density gradient for a blood flow inside the blood separator,
the microfluidic chip comprising a main channel with a microsieve to separate the blood flow into a leukocyte-rich blood fraction and a leukocyte-depleted blood fraction and to divide the main channel into first and second bifurcated channels,
wherein the leukocyte-depleted blood fraction is transported by the first bifurcated channel into an islet compartment and the leukocyte-rich blood fraction is transported by the second bifurcated channel into an exiting channel and through a blood outlet to return to the bloodstream;
(b) an islet compartment comprising multiple beta and alpha cells from at least one compatible donor pancreas;
wherein the beta and alpha cells are encapsulated within a semi-permeable, biocompatible protecting coating,
wherein the blood glucose level in the leukocyte-depleted blood is continuously monitored by the beta and alpha cells in real time,
wherein the beta cells produce an elevated level of insulin during hyperglycemia and the alpha cells produce an elevated level of glucagon when a blood glucose level of less than 60 mg/L is detected; and
(c) an exiting channel comprising a blood outlet to transport the leukocyte-depleted blood fraction, insulin and/or glucagon secreted by the beta and/or alpha cells of the islet compartment and leukocyte-rich blood fraction out of the device back into the blood stream of the human.

14. The implantable device of claim 13, wherein the density gradient for the blood flow inside the blood separator is maintained at 1.06-1.10 mg/ul.

15. The implantable device of claim 13, wherein the semi-permeable, biocompatible protecting coating encapsulating the beta and alpha cells comprises at least one material selected from the group consisting of polyacrylonitrile, polyvinylchloride, nitrocellulose acetate, 2-hydroxyethylmethacrylate (HEMA), acrylonitrile, polyacrylonitrile, sodium methalluosulfonate, alginate, hydrogel, chitosan, agarose, and cellulose.

16. The implantable device of claim 13, wherein the beta cells are activated to produce an elevated level of insulin when a blood glucose level of more than 100 mg/L is detected.

* * * * *